United States Patent
Lohse

(10) Patent No.: US 6,638,771 B1
(45) Date of Patent: Oct. 28, 2003

(54) COMPOSITION AND METHOD FOR DIAGNOSING AUTO-IMMUNE HEPATITIS

(76) Inventor: Ansgar W. Lohse, Georg-Büchner-Strasse 8, 55129 Mainz (DE)

( * ) Notice: Subject to any disclaimer, the term of this patent is extended or adjusted under 35 U.S.C. 154(b) by 0 days.

(21) Appl. No.: 09/668,286

(22) Filed: Sep. 25, 2000

Related U.S. Application Data

(62) Division of application No. 09/249,020, filed on Feb. 12, 1999.

(30) Foreign Application Priority Data

Feb. 13, 1998 (DE) .......................................... 198 05 815

(51) Int. Cl.$^7$ .................... G01N 33/566; G01N 33/567; G01N 33/564; G01N 33/543; G01N 33/53; C07K 1/00; C07K 14/00; C07K 17/00
(52) U.S. Cl. ........................ 436/503; 436/501; 436/506; 436/518; 530/350; 435/7.1
(58) Field of Search ................................ 436/501, 506, 436/507, 518, 523, 524–542, 503; 530/324, 350; 435/7.1

(56) References Cited

U.S. PATENT DOCUMENTS

| | | |
|---|---|---|
| 5,196,319 A | 3/1993 | Coppel et al. |
| 5,284,750 A | 2/1994 | Silvestrini et al. |
| 5,457,029 A | 10/1995 | Coppel et al. |
| 5,741,654 A | 4/1998 | Michel et al. |
| 5,766,867 A | 6/1998 | Mishiro et al. |
| 5,830,667 A | 11/1998 | Alvarez |
| 5,830,675 A | 11/1998 | Targan et al. |
| 5,891,436 A | 4/1999 | Coppel et al. |

OTHER PUBLICATIONS

Gruber et al. Journal of Clinical Laboratory Analysis 8:284–292.*
Manns et al., The Lancet, 1987.*
Wies et al. AASLD Abstract #112, Hepatology, Oct. 1998.*
Wies et al. GenEmbl Database Accession No. AF146396, Apr. 28, 1999.*
Ballot et al. Hepatology:AASLD Abstract 1543, Oct. 1998.*
Ando et al. Hepatology 26/4,Pt2:473A, AASLD Abstract 1378.*
Matsuoka et al. Acta Hepatologica Japionica 38/3:152–155.*
E. Ballot, et al.: "Antibodies To Soluble Liver Antigen In Auto–Immune Hepatitis Additional Oor Subtype Characteristic Marker", Hepatology, vol. 28, No. 4, pp. 1543–1544, Meeting Abstract (Oct. 1998).
Weis I. Henniger, et al. "Cloning Of The Target–Antigen Of Antibodies To Soluble Liver Antigen: Identification Of A Novel 50 kDa Protein With Two Splice–Variants", Hepatology, vol. 28, No. 4, pp. 112, Meeting Abstract (Oct. 1998).
T. Ando, et al.: "Determination Of Autoantibodies To Soluble Liver Antigen In Japanese Patients With Autoimmune Hepatitis", Hepatology, vol. 26, No. 4, pp. 1378, Meeting Abstract (Oct. 1997).
R. Gruber, et al.: "Detection Of Autoantibodies Against M2, LKM–1, And SLA In Liver Diseases By Standardized Uniform ELISA–Techniques", Journal of Clinical Laboratory Analysis, vol. 8, pp. 284–292 (1994).
Albert J. Czaja, et al.: "Antibodies To Soluble Liver Antigen, P450IID6, And Mitochondrial Complexes In Chronic Hepatitis", Gastroenterology, vol. 105, No. 25, pp. 1522–1528 (1993).
D. F. Chen, et al.: "SLA Positive Autoimmune Hepatitis Is Strongly Associated With HLA DR3", Human Immunology, Abstract, vol. 47, No. 1–2, p. P156 (1996).
A. Czaja, et al.: "Antigen–Specific Autoantibodies In Chronic Active Hepatitis: Valid Bases For Diagnostic Distinctions?", Hepatology, Meeting Abstract, vol. 16, No. 2, p. 75 (1992).
Michael P. Manns, "Cytoplasmic Autoantigens In Autoimmune Hepatitis: Molecular Analysis And Clinical Relevance", Seminars in Liver Disease, vol. 11, No. 3, pp. 205–214 (Aug. 1991).
M. Manns, et al.: "Characterisation Of A New Subgroup Of Autoimmune Chronic Active Hepatitis By Autoantibodies Against A Soluble Liver Antigen", The Lancet, pp. 292–294 (1987).
Mikio Nishioka, et al.: Antibodies To P450IID6, SLA, PDH–E2 And BEKD–E2 In Japanese Patients With Chronic Hepatitis, Journal of Gastroenterology and Hepatology, vol. 12, No. 12, pp. 862–868 (997).
T. Heintges, et al.: "Differentiation Between Autoimmune Hepatitis And Hepatitis C Virus Related Liver Disease", Z. Gastroenterologie, 1993, Bd. 31, Nr. 5, S. 285–288.

* cited by examiner

Primary Examiner—James Housel
Assistant Examiner—Zachariah Lucas
(74) Attorney, Agent, or Firm—Kenyon & Kenyon

(57) ABSTRACT

A composition and method for the diagnosis of autoimmune hepatitis. The composition, which contains SLA antigens detects soluble liver antigen (SLA) auto-antibodies, which occur in sera of patients suffering from chronic hepatitis.

10 Claims, No Drawings

COMPOSITION AND METHOD FOR DIAGNOSING AUTO-IMMUNE HEPATITIS

This is a division of application Ser. No. 09/249,020 filed Feb. 12, 1999.

BACKGROUND OF THE INVENTION

The present invention relates to a composition and method for diagnosing auto-immune hepatitis, which use an immune reaction to detect soluble liver antigen ("SLA") auto-antibodies.

Auto-immune hepatitis (AIH) is a chronic inflammation of the liver that when left untreated leads to cirrhosis, but when treated has a very good prognosis. For this reason, a timely diagnosis is important. It is estimated that 5% of all patients in Western countries who have chronic hepatitis have AIH. At the present time, there is no specific diagnostic test for AIH. Rather the diagnosis for AIH is undertaken by a plurality of diagnosis, such as excluding viral hepatitis, recognizing [hyper] immunoglobulinaemia, recognizing the tissue type (HLA type), and detecting auto-antibodies. Auto-antibodies are found in about 90% of patients with chronic hepatitis, and most of the detectable auto-antibodies are also present, at least in low titers, in other inflammations of the liver as well. In particular, these auto-antibodies are antibodies to nuclear antigens (ANA) and unstriated muscles (SMA), as well as the very rare antibodies to cytochrome p450 (LKM). SLA auto-antibodies were described for the first time in 1987 (Manns M. et al., Lancet 1987;1:292–4). Tests have shown that SLA auto-antibodies occur in about 25 to 30% of patients having AIH, but hardly ever occur in patients having other diseases, including other auto-immune diseases (Lohse A. W. et al., Z. Gastroenterol 1995;33:527–33)Detecting SLA auto-antibodies therefore provides a significant diagnostic procedure for recognizing AIH.

The present invention is directed to use and detection of SLA antigens, which are a prerequisite for developing a specific immuunoassay for detecting SLA auto-antibodies in patients' sera. Previous methods known in the art could not detect such SLA auto-antibodies in patients' sera. Liver cytokeratins 8 and 18 were described in 1990 as target antigens of the SLA auto-antibodies (Journal of Repatology, 1990; 11: 232 to 239), however, these findings were never confirmed, and were even refuted (Wies I. et al., Z. Gastroenterol. 1998;36:93).

SUMMARY OF THE INVENTION

The invention is directed to a composition for detecting the presence of SLA auto-antibodies in blood serum, said composition comprising an antigen that is recognized by SLA auto-antibodies. In particular the invention is directed to antigens having amino acid sequence SEQ ID NO:2, SEQ ID NO:4, or antigenic derivatives thereof, or encoded by DNA having DNA sequence SEQ ID NO:1, SEQ ID NO:3, or antigenic derivatives thereof. Another embodiment of the invention is a purified protein or polypeptide recognized by SLA auto-antibodies. In a preferred embodiment of the invention the purified protein has the amino acid sequence SEQ ID NO:2, SEQ ID NO:4, or antigenic derivatives thereof, or encoded by DNA having DNA sequence SEQ ID NO:1, SEQ ID NO:3, or antigenic derivatives thereof, or is a fusion protein containing either SEQ ID NO:2, SEQ ID NO:4, or antigenic derivatives thereof, or encoded by DNA having DNA sequence SEQ ID NO:1, SEQ ID NO:3, or antigenic derivatives thereof. In another aspect of the invention, there is disclosed a cDNA having a nucleotide sequence that codes for an antigen recognized by SLA auto-antibodies in blood serum. In a preferred embodiment of this aspect of the invention the cDNA codes for an antigen having the amino acid sequence SEQ ID NO:2, SEQ ID NO:4, or antigenic derivatives thereof, or has DNA sequence SEQ ID NO:1, SEQ ID NO;3, or antigenic derivatives thereof.

Another aspect of the invention is directed to a method of detecting the presence of SLA auto-antibodies in a blood sample by binding the composition of the invention to a matrix, detecting the binding of SLA auto-antibodies bound to the antigens in the composition, and correlating such binding to the presence of SLA auto-antibodies in the sample, Examples of suitable methods in which the present compositions can be used to detect SLA auto-antibodies in blood include immunoassays such as, but not limited to, radioimmunoassay, chemiluminescence, immunoassay, immunoblot assay, enzyme assay and inhibition immunoassay.

DETAILED DESCRIPTION OF THE INVENTION

The present invention relates to a composition and a method for diagnosing auto-immune hepatitis, by enabling one to detect in the blood serum of a patient, antibodies to two proteins or polypeptides (SLA antigens), which antigens wholly or partially contain the amino acid sequence corresponding to SEQ ID NO:2, SEQ ID NO:4, or antigenic derivatives thereof, or encoded by DNA having DNA sequence SEQ ID NO:1, SEQ ID NO:3, or antigenic derivatives thereof of the SLA antigens, which are recognized by SLA auto-antibodies. These polypeptides are referred to as SLA-1 and as SLA-2. One embodiment of the invention is directed to synthetic or natural variants of SLA-1 or SLA-2, or synthetic or natural variants of partial or incomplete polypeptides of SLA-1 or SLA-2, which correspond wholly or partially to the amino acid sequences or antigenic derivatives thereof and are likewise recognized by SLA auto-antibodies.

These polypeptides are referred to as SLA-1 and as SLA-2. One embodiment of the invention is directed to synthetic or natural variants of SLA-1 or SLA-2, or sythetic or natural variants of partial or incomplete polypeptides of SLA-1 or SLA-2, which correspond wholly or partially to the amino acid sequences or antigenic derivatives thereof and are likewise recognized by SLA auto-antibodies.

In a preferred embodiment, the peptides of the invention are fusion proteins. Such fusion proteins can be made by known methods in the art (Maniatis, T. et al., *Molecular Cloning*, 1982: 412–430).

Another embodiment of the invention is directed to CDNA, which encodes a natural or synthetic variant of one of the SLA antigens SLA-1or SLA-2, having a nucleotide sequence corresponding to SEQ ID NO:1 or to SEQ ID NO:3 or to antigenic derivatives thereof. The cDNAs are present as two spliced variants, the longer of these (SEQ ID NO:3) having an insertion of 156 nucleotides., SLA-1 and SLA-2 have similar nucleotide sequences, except that SLA-2 contains a 156 nucleotide insert.

SLA-positive sera, i.e. SLA auto-antibody containing sera, produces a double band on a Western blot when probed with the SLA antigens. The double band measures 50 kDa, which corresponds to the molecular weight of the SLA antigens, SLA-1 and SLA-2. When SLA-positive serum is incubated with the fusion protein according to the present invention, e.g. SLA-1 or SLA-2 fused to another protein or polypeptide, the double band corresponding to the SLA-antigen is not detected.

Incubation of SLA-positive sera with a control fusion protein, which does not contain either SLA-1 or SLA-2 does not eliminate the appearance of a double band on Western blots.

The cDNA according to the present invention allows for the production of large quantities of the SLA antigens in a recombinant fashion. Further, the concentration of SLA antigens can be measured using known SLA auto-antibody methods.

In another aspect of the invention there is disclosed a method for determining the presence of SLA auto-antibodies in a blood sample using the composition of the invention in known assay methods such as, but not limited to, radioimmunoassay (RIA), chemiluminescence immunoassay (CIA), immunoblot assay or enzyme immunoassay (EIA). In these assays, one of the SLA antigens (SLA-1or SLA-2) is bound to a matrix, such as a microtiter plate or a blot membrane. Then the patient's serum to be tested is applied to the matrix with the bound SLA antigen. Following incubation, the test serum is washed off. The specific binding of SLA auto-antibodies (in the test serum) to the matrix-bound SLA-antigen is detected and verified by using a secondary antibody (anti-human immunoglobulin or an immunoglobulin subclass, for example) that has been labeled with a tracer. Tracers commonly used include enzyme compounds such as peroxidase or alkaline phosphatase, radioactive compounds, or a chemiluminescing substances. The more SLA auto-antibodies present in the test serum, the more tracer is bound to the matrix. Normal serum from healthy blood donors can be used as a negative control. Additional controls include the use of SLA auto-antibody positive serum that has SLA auto-antibodies present at known various concentrations.

Alternatively, an inhibition immunoassay can also be performed using the SLA antigens of the present invention. In such an assay the SLA antigens bind to a selected SLA auto-antibody, which has been labeled with a tracer. The amount of binding of the labeled SLA auto-antibody to the SLA antigens is measured as the control. A patient's sera is then tested against the control. The patient's serum is added along with the labeled SLA auto-antibodies. SLA auto-antibodies present in the patient's serum compete with the labeled SLA auto-antibodies in binding to the SLA antigens. Thus, if the patient's serum contains SLA auto-antibodies, the amount of labeled SLA auto-antibodies present will be less than the control. Therefore the detection of fewer bound labeled SLA auto-antibodies reveals the presence of competing SLA auto-antibodies in the test serum.

EXAMPLE 1

Detecting SLA auto-antibodies in the ELISA test using the recombinant SLA antigen (SEQ ID No:2)

The recombinant SLA antigen was purified using the his-tag. 50 μg of the SLA antigen in 50 μl phosphate buffered saline ("PBS")(pH 7.0) was placed in a microtiter plate and left over night. After pipetting off and washing the microtiter plate, a post-coating was carried out for one hour using a 1% Bovine Serum Albumin ("BSA")/PBS solution at room temperature. 50 μl each of normal sera, patients' sera, and control sera were diluted 1:100 with PBS. 50μl of each diluted serum was incubated for 30 minutes at room temperature on its respective microtiter plate. The plates were then washed 1–5 times and a peroxidase-labeled secondary antibody, an antihuman immunoglobulin, diluted 1:8000 was then added and allowed to incubate. After washing out the excess secondary antibody, ABTS solution [55 mg of 2, 2'-azidodi-3-ethyl-benzthiazine-6-sulphonic acid (Serva, Heidelberg) in 5 ml 0.01 M $K_2HPO_4$ (pH 6.0), containing 50 μl $H_2O_2$, diluted in a 1:300 proportion in PBS] was added. The optical density of the microtiter plates was measured with a Titertec Multiscan MC (Flow Laboratories, Meckenheim). Table 1 reveals that all of the patients' sera containing SLA auto-bodies exhibited distinctly elevated values of light absorption, as compared to normal serum, and serum of patients who suffered from other liver diseases.

TABLE 1

| Serum | OD |
|---|---|
| normal serum 1 | 0.476 |
| normal serum 1 | 0.471 |
| SLA-serum 1 | 1.863 |
| SLA-serum 2 | 1.995 |
| SLA-serum 3 | 1.791 |
| SLA-serum 4 | 1.867 |
| AMA-pos. serum (PBC) | 0.615 |
| LKM-pos. serum (hep. C) | 0.769 |

Explanations: OD = optical density (extinction); AMA = anti-mitochondrial antibody; PBC = primary biliary cirrhosis; LKM = liver-kidney-microsomal; BSA = bovine serum albumin; PBS = phosphate-buffered saline

I claim:

1. A method of detecting the presence of soluble liver antigen (SLA) antibodies in a patient's blood serum comprising binding an antigen, wherein said antigen is encoded by DNA sequence SEQ ID NO:1 or has the amino acid sequence SEQ ID NO:2, that is recognized by SLA antibodies to a matrix, detecting binding of said SLA antibodies to said antigen, and correlating said binding to the presence of SLA antibodies in the patient's blood serum.

2. The method of claim 1 wherein the method is an immunoassay selected from the group consisting of radioimmunoassay, chemiluminescence immunoassay, immunoblot assay, enzyme assay and inhibition immunoassay.

3. The method of claim 1 wherein said antigen is encoded by DNA sequence SEQ ID NO:1.

4. The method of claim 1 wherein said antigen has the amino acid sequence SEQ ID NO:2.

5. The method of claim 1 wherein the antigen comprises a fusion protein comprising SEQ ID NO:2 or protein encoded by DNA sequence SEQ ID NO:1.

6. A method of detecting the presence of soluble liver antigen (SLA) antibodies in a patient's blood serum comprising binding an antigen, wherein said antigen is encoded by DNA sequence SEQ ID NO:3 or has the amino acid sequence SEQ ID NO:4, that is recognized by SLA antibodies to a matrix, detecting binding of said SLA antibodies to said antigen, and correlating said binding to the presence of SLA antibodies in the patient's blood serum.

7. The method of claim 6 wherein the method is an immunoassay selected from the group consisting of radioimmunoassay, chemiluminescence immunoassay, immunoblot assay, enzyme assay and inhibition immunoassay.

8. The method of claim 6 wherein said antigen is encoded by DNA sequence SEQ ID NO:3.

9. The method of claim 6 wherein said antigen has the amino acid sequence SEQ ID NO:4.

10. The method of claim 6 wherein the antigen comprises a fusion protein comprising SEQ ID NO:4 or a protein encoded by DNA sequence SEQ ID NO:3.

* * * * *

SEQUENCE LISTING

```
<160> NUMBER OF SEQ ID NOS: 4

<210> SEQ ID NO 1
<211> LENGTH: 1335
<212> TYPE: DNA
<213> ORGANISM: Homo sapiens
<220> FEATURE:
<221> NAME/KEY: CDS
<222> LOCATION: (1)...(1335)

<400> SEQUENCE: 1 tcg cgg cgg gag agc ggc tgg tgt cgc cgg ctt acg tgc ggc agg gct      48
Ser Arg Arg Glu Ser Gly Trp Cys Arg Arg Leu Thr Cys Gly Arg Ala
```

-continued

```
  1               5                   10                  15
gtg agg ccc gcc gct cgc atg agc acc tca tac ggc tgc ttc tgg aga      96
Val Arg Pro Ala Ala Arg Met Ser Thr Ser Tyr Gly Cys Phe Trp Arg
             20                  25                  30 agg ttc att cat ggc att gga cga tcc ggt gat att tct gct gtg caa     144
Arg Phe Ile His Gly Ile Gly Arg Ser Gly Asp Ile Ser Ala Val Gln
         35                  40                  45 cca aaa gct gca ggc tct agc ctt ttg aac aaa att acc aat tct ttg     192
Pro Lys Ala Ala Gly Ser Ser Leu Leu Asn Lys Ile Thr Asn Ser Leu
     50                  55                  60 gtc ctg gac att ata aag ctg gct ggt gtc cat aca gta gcc aac tgc     240
Val Leu Asp Ile Ile Lys Leu Ala Gly Val His Thr Val Ala Asn Cys
 65                  70                  75                  80 ttt gta gtt cct atg gca act ggt atg agt cta act ctg tgt ttc tta     288
Phe Val Val Pro Met Ala Thr Gly Met Ser Leu Thr Leu Cys Phe Leu
                 85                  90                  95 aca tta cga cac aaa aga cca aag gca aag tat att ata tgg cca cga     336
Thr Leu Arg His Lys Arg Pro Lys Ala Lys Tyr Ile Ile Trp Pro Arg
             100                 105                 110 ata gac cag aag tcc tgc ttt aaa tcc atg atc act gca ggt ttt gag     384
Ile Asp Gln Lys Ser Cys Phe Lys Ser Met Ile Thr Ala Gly Phe Glu
         115                 120                 125 cct gtg gtg ata gaa aat gtt ttg gaa ggt gac gag ctg cgt aca gac     432
Pro Val Val Ile Glu Asn Val Leu Glu Gly Asp Glu Leu Arg Thr Asp
     130                 135                 140 ctg aaa gca gtg gag gct aaa gtc cag gaa ctt ggg cct gat tgc att     480
Leu Lys Ala Val Glu Ala Lys Val Gln Glu Leu Gly Pro Asp Cys Ile
145                 150                 155                 160 ctg tgt att cat tct act aca tcc tgt ttt gct cca agg gtg cct gat     528
Leu Cys Ile His Ser Thr Thr Ser Cys Phe Ala Pro Arg Val Pro Asp
                 165                 170                 175 aga tta gaa gaa ctg gct gtg att tgt gct aat tat gac att cca cat     576
Arg Leu Glu Glu Leu Ala Val Ile Cys Ala Asn Tyr Asp Ile Pro His
             180                 185                 190 ata gtt aat aat gct tat gga gtg cag tct tca aag tgt atg cat ctc     624
Ile Val Asn Asn Ala Tyr Gly Val Gln Ser Ser Lys Cys Met His Leu
         195                 200                 205 att cag cag ggg gct cga gtt ggt aga ata gat gct ttt gtt cag agc     672
Ile Gln Gln Gly Ala Arg Val Gly Arg Ile Asp Ala Phe Val Gln Ser
     210                 215                 220 ttg gac aaa aat ttt atg gtt cca gta ggt ggt gct ata att gct ggc     720
Leu Asp Lys Asn Phe Met Val Pro Val Gly Gly Ala Ile Ile Ala Gly
225                 230                 235                 240 ttt aat gat tca ttc att cag gaa atc agc aag atg tat cca gga aga     768
Phe Asn Asp Ser Phe Ile Gln Glu Ile Ser Lys Met Tyr Pro Gly Arg
                 245                 250                 255 gct tca gct tca cct tct tta gat gtc ctt att act tta ttg tca ctt     816
Ala Ser Ala Ser Pro Ser Leu Asp Val Leu Ile Thr Leu Leu Ser Leu
             260                 265                 270 gga tca aat ggc tat aag aag cta cta aaa gaa aga aag gaa atg ttt     864
Gly Ser Asn Gly Tyr Lys Lys Leu Leu Lys Glu Arg Lys Glu Met Phe
         275                 280                 285 tca tat ttg tcc aac caa ata aag aag ttg tca gaa gcc tac aat gaa     912
Ser Tyr Leu Ser Asn Gln Ile Lys Lys Leu Ser Glu Ala Tyr Asn Glu
     290                 295                 300 aga ctg ttg cat aca cct cac aat ccc ata tct tta gct atg aca ctt     960
Arg Leu Leu His Thr Pro His Asn Pro Ile Ser Leu Ala Met Thr Leu
305                 310                 315                 320 aaa aca cta gat gaa cac cgt gac aaa gct gtc act cag ctt ggc tcg    1008
```

-continued

```
Lys Thr Leu Asp Glu His Arg Asp Lys Ala Val Thr Gln Leu Gly Ser
            325                 330                 335 atg ctt ttt acc aaa cag gtt tct gga gcc agg gtt gtg cct ctt ggg      1056
Met Leu Phe Thr Lys Gln Val Ser Gly Ala Arg Val Val Pro Leu Gly
            340                 345                 350 tcc atg caa act gtg agt ggc tat act ttc aga ggc ttt atg tca cat      1104
Ser Met Gln Thr Val Ser Gly Tyr Thr Phe Arg Gly Phe Met Ser His
            355                 360                 365 aca aat aat tac cct tgt gct tac ctc aat gct gca tca gcc atc gga      1152
Thr Asn Asn Tyr Pro Cys Ala Tyr Leu Asn Ala Ala Ser Ala Ile Gly
        370                 375                 380 atg aar atg cag gat gtg gac ctg ttc ata aac ara ctt gac agg tgt      1200
Met Lys Met Gln Asp Val Asp Leu Phe Ile Asn Xaa Leu Asp Arg Cys
385                 390                 395                 400 tta aag gca gta aga aaa gaa cga agt aaa gag agt gat gac aat tat      1248
Leu Lys Ala Val Arg Lys Glu Arg Ser Lys Glu Ser Asp Asp Asn Tyr
                405                 410                 415 gac aaa act gaa rat gtg gat att gaa gaa atg gct tta aaa cta gat      1296
Asp Lys Thr Glu Xaa Val Asp Ile Glu Glu Met Ala Leu Lys Leu Asp
            420                 425                 430 aat gta ctt ctt gac aca tac cag gat gct tct tca tga                  1335
Asn Val Leu Leu Asp Thr Tyr Gln Asp Ala Ser Ser  *
            435                 440
```

<210> SEQ ID NO 2
<211> LENGTH: 444
<212> TYPE: PRT
<213> ORGANISM: Homo sapiens
<220> FEATURE:
<221> NAME/KEY: VARIANT
<222> LOCATION: (1)...(444)
<223> OTHER INFORMATION: Xaa = Any Amino Acid

<400> SEQUENCE: 2

```
Ser Arg Arg Glu Ser Gly Trp Cys Arg Arg Leu Thr Cys Gly Arg Ala
 1               5                  10                  15

Val Arg Pro Ala Ala Arg Met Ser Thr Ser Tyr Gly Cys Phe Trp Arg
            20                  25                  30

Arg Phe Ile His Gly Ile Gly Arg Ser Gly Asp Ile Ser Ala Val Gln
        35                  40                  45

Pro Lys Ala Ala Gly Ser Ser Leu Leu Asn Lys Ile Thr Asn Ser Leu
    50                  55                  60

Val Leu Asp Ile Ile Lys Leu Ala Gly Val His Thr Val Ala Asn Cys
65                  70                  75                  80

Phe Val Val Pro Met Ala Thr Gly Met Ser Leu Thr Leu Cys Phe Leu
                85                  90                  95

Thr Leu Arg His Lys Arg Pro Lys Ala Lys Tyr Ile Ile Trp Pro Arg
            100                 105                 110

Ile Asp Gln Lys Ser Cys Phe Lys Ser Met Ile Thr Ala Gly Phe Glu
        115                 120                 125

Pro Val Val Ile Glu Asn Val Leu Glu Gly Asp Glu Leu Arg Thr Asp
    130                 135                 140

Leu Lys Ala Val Glu Ala Lys Val Gln Glu Leu Gly Pro Asp Cys Ile
145                 150                 155                 160

Leu Cys Ile His Ser Thr Thr Ser Cys Phe Ala Pro Arg Val Pro Asp
                165                 170                 175

Arg Leu Glu Glu Leu Ala Val Ile Cys Ala Asn Tyr Asp Ile Pro His
            180                 185                 190
```

-continued

```
Ile Val Asn Asn Ala Tyr Gly Val Gln Ser Ser Lys Cys Met His Leu
            195                 200                 205

Ile Gln Gln Gly Ala Arg Val Gly Arg Ile Asp Ala Phe Val Gln Ser
    210                 215                 220

Leu Asp Lys Asn Phe Met Val Pro Val Gly Ala Ile Ile Ala Gly
225                 230                 235                 240

Phe Asn Asp Ser Phe Ile Gln Glu Ile Ser Lys Met Tyr Pro Gly Arg
                245                 250                 255

Ala Ser Ala Ser Pro Ser Leu Asp Val Leu Ile Thr Leu Leu Ser Leu
                260                 265                 270

Gly Ser Asn Gly Tyr Lys Lys Leu Leu Lys Glu Arg Lys Glu Met Phe
            275                 280                 285

Ser Tyr Leu Ser Asn Gln Ile Lys Lys Leu Ser Glu Ala Tyr Asn Glu
    290                 295                 300

Arg Leu Leu His Thr Pro His Asn Pro Ile Ser Leu Ala Met Thr Leu
305                 310                 315                 320

Lys Thr Leu Asp Glu His Arg Asp Lys Ala Val Thr Gln Leu Gly Ser
                325                 330                 335

Met Leu Phe Thr Lys Gln Val Ser Gly Ala Arg Val Val Pro Leu Gly
                340                 345                 350

Ser Met Gln Thr Val Ser Gly Tyr Thr Phe Arg Gly Phe Met Ser His
            355                 360                 365

Thr Asn Asn Tyr Pro Cys Ala Tyr Leu Asn Ala Ala Ser Ala Ile Gly
    370                 375                 380

Met Lys Met Gln Asp Val Asp Leu Phe Ile Asn Xaa Leu Asp Arg Cys
385                 390                 395                 400

Leu Lys Ala Val Arg Lys Glu Arg Ser Lys Glu Ser Asp Asp Asn Tyr
                405                 410                 415

Asp Lys Thr Glu Xaa Val Asp Ile Glu Glu Met Ala Leu Lys Leu Asp
            420                 425                 430

Asn Val Leu Leu Asp Thr Tyr Gln Asp Ala Ser Ser
            435                 440

<210> SEQ ID NO 3
<211> LENGTH: 1491
<212> TYPE: DNA
<213> ORGANISM: Homo sapiens
<220> FEATURE:
<221> NAME/KEY: CDS
<222> LOCATION: (1)...(1491)
<221> NAME/KEY: misc_feature
<222> LOCATION: (1)...(1491)
<223> OTHER INFORMATION: n = A,T,C or G

<400> SEQUENCE: 3 tcg cgg cgg gag agc ggc tgg tgt cgc cgg ctt acg tgc ggc agg gct      48
Ser Arg Arg Glu Ser Gly Trp Cys Arg Arg Leu Thr Cys Gly Arg Ala
 1               5                  10                  15 gtg agg ccc gcc gct cgc atg agc acc tca tac ggc tgc ttc tgg aga      96
Val Arg Pro Ala Ala Arg Met Ser Thr Ser Tyr Gly Cys Phe Trp Arg
             20                  25                  30 agg gcw nnn tgt cca aag aat ggc tgg gat gaa agt aca ctt gaa ctc     144
Arg Xaa Xaa Cys Pro Lys Asn Gly Trp Asp Glu Ser Thr Leu Glu Leu
         35                  40                  45 ttt tta cat gaa ctt gca atc atg gac agc aac aat ttc tta ggc aat     192
Phe Leu His Glu Leu Ala Ile Met Asp Ser Asn Asn Phe Leu Gly Asn
     50                  55                  60 tgt ggt gtg gga gaa agg gaa ggg aga gtg gca tcc gca ctg gtt gct     240
```

|  |  |  |  |  |  |  |  |  |  |  |  |  |  |  |  |
|---|---|---|---|---|---|---|---|---|---|---|---|---|---|---|---|
| Cys | Gly | Val | Gly | Glu | Arg | Glu | Gly | Arg | Val | Ala | Ser | Ala | Leu | Val | Ala |
| 65 |  |  |  |  | 70 |  |  |  | 75 |  |  |  |  | 80 |  |

```
cgt cgt cat tac agg ttc att cat ggc att gga cga tcc ggt gat att        288
Arg Arg His Tyr Arg Phe Ile His Gly Ile Gly Arg Ser Gly Asp Ile
                    85                  90                  95 tct gct gtg caa cca aaa gct gca ggc tct agc ctt ttg aac aaa att        336
Ser Ala Val Gln Pro Lys Ala Ala Gly Ser Ser Leu Leu Asn Lys Ile
                100                 105                 110 acc aat tct ttg gtc ctg gac att ata aag ctg gct ggt gtc cat aca        384
Thr Asn Ser Leu Val Leu Asp Ile Ile Lys Leu Ala Gly Val His Thr
                115                 120                 125 gta gcc aac tgc ttt gta gtt cct atg gca act ggt atg agt cta act       432
Val Ala Asn Cys Phe Val Val Pro Met Ala Thr Gly Met Ser Leu Thr
        130                 135                 140 ctg tgt ttc tta aca tta cga cac aaa aga cca aag gca aag tat att       480
Leu Cys Phe Leu Thr Leu Arg His Lys Arg Pro Lys Ala Lys Tyr Ile
145                 150                 155                 160 ata tgg cca cga ata gac cag aag tcc tgc ttt aaa tcc atg atc act       528
Ile Trp Pro Arg Ile Asp Gln Lys Ser Cys Phe Lys Ser Met Ile Thr
                    165                 170                 175 gca ggt ttt gag cct gtg gtg ata gaa aat gtt ttg gaa ggt gac gag       576
Ala Gly Phe Glu Pro Val Val Ile Glu Asn Val Leu Glu Gly Asp Glu
                180                 185                 190 ctg cgt aca gac ctg aaa gca gtg gag gct aaa gtc cag gaa ctt ggg       624
Leu Arg Thr Asp Leu Lys Ala Val Glu Ala Lys Val Gln Glu Leu Gly
            195                 200                 205 cct gat tgc att ctg tgt att cat tct act aca tcc tgt ttt gct cca       672
Pro Asp Cys Ile Leu Cys Ile His Ser Thr Thr Ser Cys Phe Ala Pro
        210                 215                 220 agg gtg cct gat aga tta gaa gaa ctg gct gtg att tgt gct aat tat       720
Arg Val Pro Asp Arg Leu Glu Glu Leu Ala Val Ile Cys Ala Asn Tyr
225                 230                 235                 240 gac att cca cat ata gtt aat aat gct tat gga gtg cag tct tca aag       768
Asp Ile Pro His Ile Val Asn Asn Ala Tyr Gly Val Gln Ser Ser Lys
                245                 250                 255 tgt atg cat ctc att cag cag ggg gct cga gtt ggt aga ata gat gct       816
Cys Met His Leu Ile Gln Gln Gly Ala Arg Val Gly Arg Ile Asp Ala
                260                 265                 270 ttt gtt cag agc ttg gac aaa aat ttt atg gtt cca gta ggt ggt gct       864
Phe Val Gln Ser Leu Asp Lys Asn Phe Met Val Pro Val Gly Gly Ala
            275                 280                 285 ata att gct ggc ttt aat gat tca ttc att cag gaa atc agc aag atg       912
Ile Ile Ala Gly Phe Asn Asp Ser Phe Ile Gln Glu Ile Ser Lys Met
        290                 295                 300 tat cca gga aga gct tca gct tca cct tct tta gat gtc ctt att act       960
Tyr Pro Gly Arg Ala Ser Ala Ser Pro Ser Leu Asp Val Leu Ile Thr
305                 310                 315                 320 tta ttg tca ctt gga tca aat ggc tat aag aag cta cta aaa gaa aga      1008
Leu Leu Ser Leu Gly Ser Asn Gly Tyr Lys Lys Leu Leu Lys Glu Arg
                325                 330                 335 aag gaa atg ttt tca tat ttg tcc aac caa ata aag aag ttg tca gaa      1056
Lys Glu Met Phe Ser Tyr Leu Ser Asn Gln Ile Lys Lys Leu Ser Glu
                340                 345                 350 gcc tac aat gaa aga ctg ttg cat aca cct cac aat ccc ata tct tta      1104
Ala Tyr Asn Glu Arg Leu Leu His Thr Pro His Asn Pro Ile Ser Leu
            355                 360                 365 gct atg aca ctt aaa aca cta gat gaa cac cgt gac aaa gct gtc act      1152
Ala Met Thr Leu Lys Thr Leu Asp Glu His Arg Asp Lys Ala Val Thr
        370                 375                 380
```

-continued

```
cag ctt ggc tcg atg ctt ttt acc aaa cag gtt tct gga gcc agg gtt       1200
Gln Leu Gly Ser Met Leu Phe Thr Lys Gln Val Ser Gly Ala Arg Val
385                 390                 395                 400 gtg cct ctt ggg tcc atg caa act gtg agt ggc tat act ttc aga ggc       1248
Val Pro Leu Gly Ser Met Gln Thr Val Ser Gly Tyr Thr Phe Arg Gly
                405                 410                 415 ttt atg tca cat aca aat aat tac cct tgt gct tac ctc aat gct gca       1296
Phe Met Ser His Thr Asn Asn Tyr Pro Cys Ala Tyr Leu Asn Ala Ala
            420                 425                 430 tca gcc atc gga atg aar atg cag gat gtg gac ctg ttc ata aac ara       1344
Ser Ala Ile Gly Met Lys Met Gln Asp Val Asp Leu Phe Ile Asn Xaa
                435                 440                 445 ctt gac agg tgt tta aag gca gta aga aaa gaa cga agt aaa gag agt       1392
Leu Asp Arg Cys Leu Lys Ala Val Arg Lys Glu Arg Ser Lys Glu Ser
450                 455                 460 gat gac aat tat gac aaa act gaa rat gtg gat att gaa gaa atg gct       1440
Asp Asp Asn Tyr Asp Lys Thr Glu Xaa Val Asp Ile Glu Glu Met Ala
465                 470                 475                 480 tta aaa cta gat aat gta ctt ctt gac aca tac cag gat gct tct tca       1488
Leu Lys Leu Asp Asn Val Leu Leu Asp Thr Tyr Gln Asp Ala Ser Ser
                485                 490                 495 tga                                                                    1491
*
```

<210> SEQ ID NO 4
<211> LENGTH: 496
<212> TYPE: PRT
<213> ORGANISM: Homo sapiens
<220> FEATURE:
<221> NAME/KEY: VARIANT
<222> LOCATION: (1)...(496)
<223> OTHER INFORMATION: Xaa = Any Amino Acid

<400> SEQUENCE: 4

```
Ser Arg Arg Glu Ser Gly Trp Cys Arg Arg Leu Thr Cys Gly Arg Ala
1               5                   10                  15

Val Arg Pro Ala Ala Arg Met Ser Thr Ser Tyr Gly Cys Phe Trp Arg
                20                  25                  30

Arg Xaa Xaa Cys Pro Lys Asn Gly Trp Asp Glu Ser Thr Leu Glu Leu
            35                  40                  45

Phe Leu His Glu Leu Ala Ile Met Asp Ser Asn Asn Phe Leu Gly Asn
    50                  55                  60

Cys Gly Val Gly Glu Arg Glu Gly Arg Val Ala Ser Ala Leu Val Ala
65                  70                  75                  80

Arg Arg His Tyr Arg Phe Ile His Gly Ile Gly Arg Ser Gly Asp Ile
                85                  90                  95

Ser Ala Val Gln Pro Lys Ala Ala Gly Ser Ser Leu Leu Asn Lys Ile
                100                 105                 110

Thr Asn Ser Leu Val Leu Asp Ile Ile Lys Leu Ala Gly Val His Thr
            115                 120                 125

Val Ala Asn Cys Phe Val Val Pro Met Ala Thr Gly Met Ser Leu Thr
    130                 135                 140

Leu Cys Phe Leu Thr Leu Arg His Lys Arg Pro Lys Ala Lys Tyr Ile
145                 150                 155                 160

Ile Trp Pro Arg Ile Asp Gln Lys Ser Cys Phe Lys Ser Met Ile Thr
                165                 170                 175

Ala Gly Phe Glu Pro Val Val Ile Glu Asn Val Leu Glu Gly Asp Glu
                180                 185                 190
```

-continued

```
Leu Arg Thr Asp Leu Lys Ala Val Glu Ala Lys Val Gln Glu Leu Gly
    195                 200                 205

Pro Asp Cys Ile Leu Cys Ile His Ser Thr Thr Ser Cys Phe Ala Pro
    210                 215                 220

Arg Val Pro Asp Arg Leu Glu Glu Leu Ala Val Ile Cys Ala Asn Tyr
225                 230                 235                 240

Asp Ile Pro His Ile Val Asn Asn Ala Tyr Gly Val Gln Ser Ser Lys
            245                 250                 255

Cys Met His Leu Ile Gln Gln Gly Ala Arg Val Gly Arg Ile Asp Ala
            260                 265                 270

Phe Val Gln Ser Leu Asp Lys Asn Phe Met Val Pro Val Gly Gly Ala
        275                 280                 285

Ile Ile Ala Gly Phe Asn Asp Ser Phe Ile Gln Glu Ile Ser Lys Met
    290                 295                 300

Tyr Pro Gly Arg Ala Ser Ala Ser Pro Ser Leu Asp Val Leu Ile Thr
305                 310                 315                 320

Leu Leu Ser Leu Gly Ser Asn Gly Tyr Lys Lys Leu Leu Lys Glu Arg
                325                 330                 335

Lys Glu Met Phe Ser Tyr Leu Ser Asn Gln Ile Lys Lys Leu Ser Glu
            340                 345                 350

Ala Tyr Asn Glu Arg Leu Leu His Thr Pro His Asn Pro Ile Ser Leu
            355                 360                 365

Ala Met Thr Leu Lys Thr Leu Asp Glu His Arg Asp Lys Ala Val Thr
370                 375                 380

Gln Leu Gly Ser Met Leu Phe Thr Lys Gln Val Ser Gly Ala Arg Val
385                 390                 395                 400

Val Pro Leu Gly Ser Met Gln Thr Val Ser Gly Tyr Thr Phe Arg Gly
                405                 410                 415

Phe Met Ser His Thr Asn Asn Tyr Pro Cys Ala Tyr Leu Asn Ala Ala
                420                 425                 430

Ser Ala Ile Gly Met Lys Met Gln Asp Val Asp Leu Phe Ile Asn Xaa
            435                 440                 445

Leu Asp Arg Cys Leu Lys Ala Val Arg Lys Glu Arg Ser Lys Glu Ser
    450                 455                 460

Asp Asp Asn Tyr Asp Lys Thr Glu Xaa Val Asp Ile Glu Glu Met Ala
465                 470                 475                 480

Leu Lys Leu Asp Asn Val Leu Leu Asp Thr Tyr Gln Asp Ala Ser Ser
                485                 490                 495
```